United States Patent
Cinader, Jr. et al.

(10) Patent No.: US 7,452,205 B2
(45) Date of Patent: Nov. 18, 2008

(54) ORTHODONTIC INDIRECT BONDING APPARATUS WITH OCCLUSAL POSITIONING STOP MEMBERS

(75) Inventors: David K. Cinader, Jr., Yorba Linda, CA (US); James K. Mah, Hermosa Beach, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 626 days.

(21) Appl. No.: 11/098,716

(22) Filed: Apr. 4, 2005

(65) Prior Publication Data

US 2006/0223021 A1 Oct. 5, 2006

(51) Int. Cl.
*A61C 3/00* (2006.01)
(52) U.S. Cl. ............................................. 433/24; 433/3
(58) Field of Classification Search ...................... 433/8, 433/9, 24, 213
See application file for complete search history.

(56) References Cited

U.S. PATENT DOCUMENTS

| | | | |
|---|---|---|---|
| 4,501,554 A | 2/1985 | Hickham | |
| 4,551,096 A | 11/1985 | Dellinger | |
| 4,657,508 A | 4/1987 | Dellinger | |
| 5,015,180 A | 5/1991 | Randklev | |
| 5,172,809 A | 12/1992 | Jacobs et al. | |
| 5,354,199 A | 10/1994 | Jacobs et al. | |
| 5,429,229 A | 7/1995 | Chester et al. | |
| 5,863,198 A | 1/1999 | Doyle | |
| 5,971,754 A | 10/1999 | Sondhi et al. | |
| 6,045,359 A * | 4/2000 | Tucker | 433/37 |
| 6,123,544 A | 9/2000 | Cleary | |
| 6,174,163 B1 | 1/2001 | Hiro | |
| 6,302,688 B1 | 10/2001 | Jordan et al. | |
| 6,607,382 B1 | 8/2003 | Kuo et al. | |
| 6,705,863 B2 | 3/2004 | Phan et al. | |
| 2002/0028417 A1 | 3/2002 | Chapoulaud et al. | |
| 2003/0163291 A1 | 8/2003 | Jordan et al. | |
| 2004/0219471 A1 | 11/2004 | Cleary et al. | |
| 2004/0219473 A1 | 11/2004 | Cleary et al. | |
| 2005/0074716 A1 | 4/2005 | Cleary et al. | |
| 2005/0133384 A1 | 6/2005 | Cinader et al. | |

FOREIGN PATENT DOCUMENTS

| | | |
|---|---|---|
| WO | WO 01/85047 | 11/2001 |
| WO | WO 02/089693 | 11/2002 |

OTHER PUBLICATIONS

JCO/Mar. 2003; The Hybrid Core System for Indirect Bonding, Matsuno et al., pp. 160-161.

(Continued)

*Primary Examiner*—John J Wilson
*Assistant Examiner*—Heidi M Bashaw
(74) *Attorney, Agent, or Firm*—James D. Christoff

(57) ABSTRACT

A transfer apparatus for indirect bonding of orthodontic appliances includes a tray with a channel and a matrix material received in the channel. At least one stop member is connected to the tray and is made of a relatively rigid thermoset material. Each stop member helps to facilitate accurate positioning of the tray in the patient's oral cavity during a bonding procedure, a particular advantage when the matrix material is relatively flexible.

22 Claims, 5 Drawing Sheets

OTHER PUBLICATIONS

Morita Europe, Demonstration Models, Apr. 24, 2003, www.jmoritaeurope.de/DemomodelsEng.html, 8 pages.

Moskowitz et al., A New Look at Indirect Bonding, Journal of Clinical Orthodontics, 1996, vol. XXX No. 5, pp. 277-281.

Hickham, Predictable Indirect Bonding, Journal of Clinical Orthodontics, 1993, vol. XXVII, No. 4, pp. 215-217.

Sinha et al., A Thermal-Cured Fluoride-Releasing Indirect Bonding System, Journal of Clinical Orthodontics, 1995, vol. XXIX, No. 2, pp. 97-100.

Cooper et al., Indirect Bonding with Adhesive Precoated Brackets, Journal of Clinical Orthodontics, Mar. 1993, vol. XXVII, No. 3, pp. 164-167.

Kasrovi, A New Approach To Indirect Bonding Using Light-Cure Composites, American Journal of Orthodontics and Dentofacial Orthopedics, Jun. 1997, pp. 652-656.

Reichheld et al., An Indirect Bonding Technique, Journal of Clinical Orthodontics, 1990, vol. XXIV, No. 1, pp. 21-24.

Pending U.S. Appl. No. 11/098,317, filed Apr. 4, 2005.

* cited by examiner

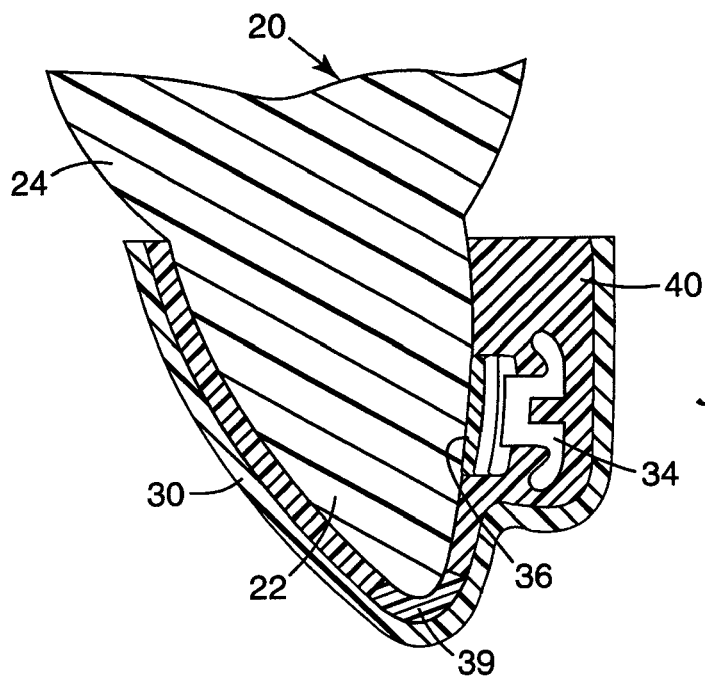
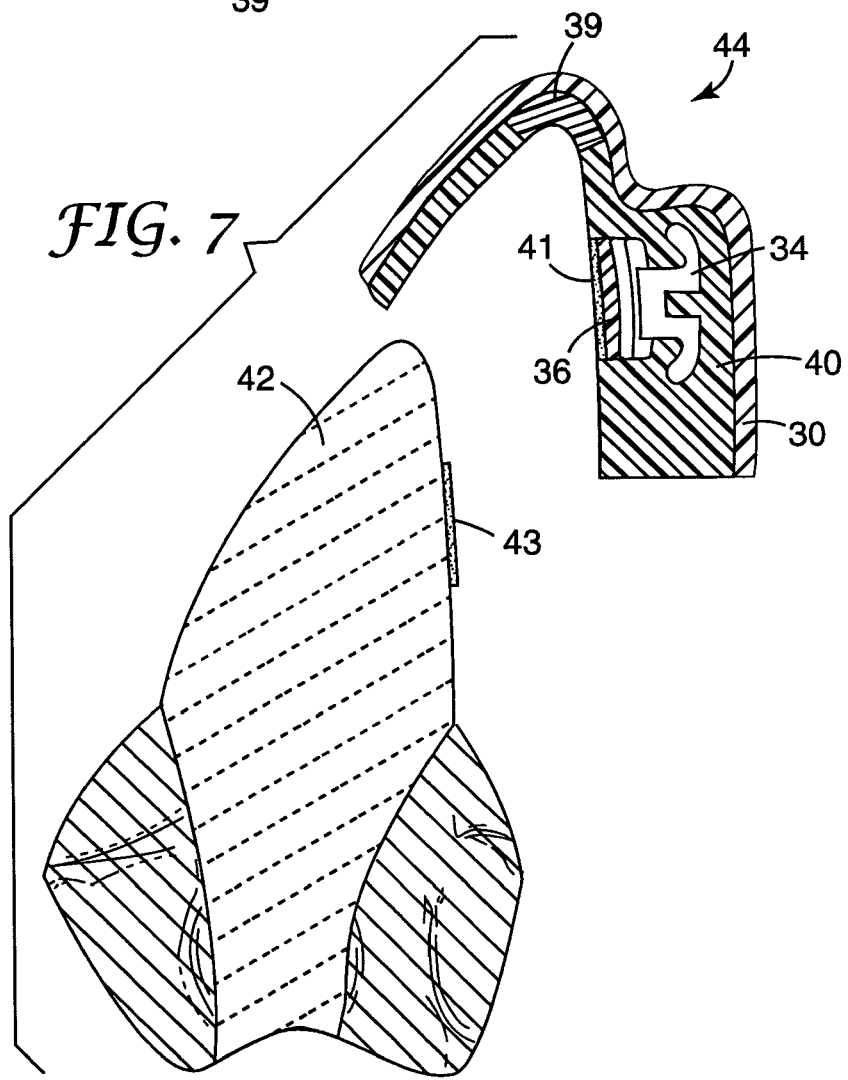
FIG. 6
FIG. 7

ORTHODONTIC INDIRECT BONDING APPARATUS WITH OCCLUSAL POSITIONING STOP MEMBERS

BACKGROUND OF THE INVENTION

1. Field of the Invention

This invention relates to method and apparatus for bonding orthodontic appliances such as brackets to a patient's teeth. The present invention also relates to methods for indirect bonding of orthodontic appliances.

2. Description of the Related Art

Orthodontic treatment involves movement of malpositioned teeth to desired locations in the oral cavity. Orthodontic treatment can improve the patient's facial appearance, especially in instances where the teeth are noticeably crooked or where the jaws are out of alignment with each other. Orthodontic treatment can also enhance the function of the teeth by providing better occlusion during mastication.

One common type of orthodontic treatment involves the use of tiny, slotted appliances known as brackets. The brackets are fixed to the patient's teeth and an archwire is placed in the slot of each bracket. The archwire forms a track to guide movement of teeth to desired locations.

The ends of orthodontic archwires are often connected to small appliances known as buccal tubes that are, in turn, secured to the patient's molar teeth. In many instances, a set of brackets, buccal tubes and an archwire is provided for each of the patient's upper and lower dental arches. The brackets, buccal tubes and archwires are commonly referred to collectively as "braces".

In many types of orthodontic techniques, the precise position of the appliances on the teeth is an important factor for helping to ensure that the teeth move to their intended final positions. For example, one common type of orthodontic treatment technique is known as the "straight-wire" technique, where the archwire lies in a horizontal plane at the conclusion of treatment. Consequently, if a bracket is attached to the tooth at a location that is too close to the occlusal or outer tip of the tooth, the orthodontist using a straight-wire technique will likely find that the tooth in its final position is unduly intruded. On the other hand, if the bracket is attached to the tooth at a location closer to the gingiva than is appropriate, it is likely that the final position of the tooth will be more extruded than desired.

In general, orthodontic appliances that are adapted to be adhesively bonded to the patient's teeth are placed and connected to the teeth by either one of two techniques: a direct bonding technique, or an indirect bonding technique. In the direct bonding technique, the appliance and adhesive are grasped with a pair of tweezers or other hand instrument and placed by the practitioner on the surface of the tooth in an approximate desired location. Next, the appliance is shifted along the surface of the tooth as needed until the practitioner is satisfied with its position. Once the appliance is in its precise, intended location, the appliance is pressed firmly onto the tooth to seat the appliance in the adhesive. Excess adhesive in areas adjacent the base of the appliance is removed, and the adhesive is then allowed to cure and fix the appliance firmly in place.

While the direct bonding technique described above is in widespread use and is considered satisfactory by many, there are shortcomings that are inherent with this technique. For example, access to surfaces of malposed teeth may be difficult. In some instances, and particularly in connection with posterior teeth, the practitioner may have difficulty seeing the precise position of the bracket relative to the tooth surface. Additionally, the appliance may be unintentionally dislodged from its intended location during the time that the excess adhesive is being removed adjacent the base of the appliance.

Another problem associated with the direct bonding technique described above concerns the significant length of time needed to carry out the procedure of bonding each appliance to each individual tooth. Typically, the practitioner will attempt to ensure that each appliance is positioned in its precise, intended location before the adhesive is cured, and some amount of time may be necessary before the practitioner is satisfied with the location of each appliance. At the same time, however, the patient may experience discomfort during the procedure and have difficulty in remaining relatively motionless, especially if the patient is an adolescent. As can be appreciated, there are aspects of the direct bonding technique that can be considered a nuisance for both the practitioner and for the patient.

Indirect bonding techniques avoid many of the problems noted above. In general, indirect bonding techniques known in the past have involved the use of a placement device or transfer apparatus having a shape that matches the configuration of at least part of the patient's dental arch. One type of placement device or transfer apparatus is often called a "transfer tray" and typically has a cavity for receiving a number of teeth simultaneously. A set of appliances such as brackets are releasably connected to the tray at certain, predetermined locations.

Other types of transfer apparatus used in indirect bonding are often referred to as "jigs" and resemble a framework that contacts one or more teeth at certain locations. For example, a jig constructed for use in bonding a single appliance to a single tooth may have an arm that extends over and contacts an incisal section of the tooth. An appliance such as a bracket is releasably connected to the jig at a certain, predetermined location relative to the tooth.

During the use of orthodontic transfer apparatus for indirect bonding, an adhesive is typically applied to the base of each appliance by the orthodontist or a staff member. The device is then placed over the patient's teeth and remains in place until such time as the adhesive hardens. Next, the apparatus is detached from the teeth as well as from the appliances, with the result that all of the appliances previously connected to the apparatus are now bonded to respective teeth at their intended, predetermined locations.

In more detail, one method of indirect bonding of orthodontic appliances using the transfer tray described above includes the steps of taking an impression of each of the patient's dental arches and then making a replica plaster or "stone" model from each impression. Next, the appliances are bonded to the stone models at desired locations. Optionally, the bonding adhesive can be a chemical curing adhesive (such as Concise brand adhesive from 3M) or a light-curable adhesive (such as Transbond XT brand adhesive or Transbond LR brand adhesive from 3M). Optionally, the brackets may be adhesive precoated brackets such as those described in U.S. Pat. Nos. 5,015,180, 5,172,809, 5,354,199 and 5,429,229.

The transfer tray is then made by placing a matrix material over the model as well as over the appliances placed in the model. For example, a plastic sheet matrix material may be held by a frame and exposed to radiant heat. Once the plastic sheet material has softened, it is placed over the model and the appliances. Air in the space between the sheet material and the model is then evacuated, and the plastic sheet material assumes a configuration that precisely matches the shape of the replica teeth of the stone model and attached appliances.

The plastic sheet matrix material is then allowed to cool and harden to form a tray. The tray and the appliances (which are embedded in an interior wall of the tray) are then detached from the stone model. If the cured adhesive that was used to bond the appliances to the stone model remains on the base of the appliances after detachment from the stone model, the adhesive serves as a "custom" base having a concave contour that precisely replicates the convex contour of the previous attachment location of the stone model, as well as the convex configuration of the intended mounting location of the appliances on the patient's teeth.

Once the patient has returned to the practitioner's office, a quantity of adhesive is placed on the base of each appliance, and the tray with the embedded appliances is then placed over the matching portions of the patient's dental arch. Since the configuration of the interior of the tray closely matches the respective portions of the patient's dental arch, each appliance is ultimately positioned on the patient's teeth at precisely the same location that corresponds to the previous location of the same appliance on the stone model.

Indirect bonding techniques offer a number of advantages over direct bonding techniques. For one thing, and as indicated above, it is possible to bond a plurality of appliances to a patient's dental arch simultaneously, thereby avoiding the need to bond each appliance in individual fashion. In addition, the transfer apparatus helps to locate the appliances in their proper, intended positions such that adjustment of each appliance on the surface of the tooth before bonding is avoided. The increased placement accuracy of the appliances that is often afforded by indirect bonding techniques helps ensure that the patient's teeth are moved to their proper, intended positions at the conclusion of treatment.

In recent years, many improvements have been made in the field of indirect bonding. For example, U.S. Pat. No. 5,971,754 describes a two-component indirect bonding adhesive with a relatively fast curing time that reduces the length of time that the tray must be firmly held against the patient's teeth. U.S. Pat. No. 6,123,544 describes a transfer tray that receives movable arms for placing appliances on the patient's teeth once the tray is positioned in the oral cavity. Published U.S. patent application entitled "METHOD AND APPARATUS FOR INDIRECT BONDING OF ORTHODONTIC APPLIANCES" (U.S. Publication No. 2004-0219471, published on Nov. 4, 2004), describes among other things a transfer apparatus with an improved matrix material for releasably holding appliances in place. Published U.S. patent application entitled "APPARATUS FOR INDIRECT BONDING OF ORTHODONTIC APPLIANCES AND METHOD OF MAKING THE SAME" (U.S. No. 2005/0074716, published Apr. 7, 2005) describes among other things a transfer apparatus that includes at least one appliance having a base with a contour that is a replica of a contour of a portions of the patient's tooth structure, and a bonding composition on the base for bonding to the patient's tooth structure.

Although the improvements described above in the field of orthodontic indirect bonding are significant, there is a continuing need to improve the accuracy of the placement of the appliances on the patient's dental arch in order to help ensure that the patient's teeth are located in their precise, intended orientations at the conclusion of treatment. A skilled orthodontist can often compensate for minor erroneous placement of the bonded appliances. However, it is best to place the appliances as accurately as possible so that such compensation is not needed.

SUMMARY OF THE INVENTION

The present invention is directed toward an improved indirect bonding transfer apparatus that includes one or more relatively rigid occlusal stop members. As the apparatus is placed over the patient's dental arch, the occlusal stop members engage one or more occlusal sections of the patient's dental arch as the appliance or appliances are positioned on the patient's tooth structure. Each of the occlusal stop members helps to accurately position the appliance with respect to the patient's tooth structure. As a result, the accuracy of placement of the bonded appliance is increased even when certain components of the transfer apparatus are comprised of relatively flexible material.

In more detail, the present invention in one aspect is directed toward a transfer apparatus for use in indirect bonding of orthodontic appliances. The apparatus comprises a tray having a channel with a bottom wall portion. The transfer apparatus also includes a matrix material that is received in the channel. The transfer apparatus further includes at least one orthodontic appliance that is detachably connected to the matrix material, and the matrix material has a first Shore hardness. The transfer apparatus also includes at least one stop member located next to the bottom wall portion of the tray. Each stop member comprises a polymeric thermoset material having a second Shore hardness that is greater than the first Shore hardness, and extends next to the matrix material for contact with an occlusal section of the dental arch.

Another aspect of the present invention is directed toward a method of orthodontic indirect bonding. The method comprises:

providing an orthodontic transfer apparatus comprising a tray, a quantity of matrix material received in the tray, and one or more orthodontic appliances detachably connected to the matrix material, wherein the matrix material has a first Shore hardness;

moving the transfer apparatus into the patient's oral cavity in order to locate one or more orthodontic appliances adjacent the patient's dental arch; and engaging a thermoset polymeric material of the transfer apparatus with an occlusal section of the patient's dental arch as one or more of the appliances are brought into contact with the patient's dental arch, wherein the thermoset polymeric material has a second Shore hardness that is greater than the first Shore hardness of the matrix material.

Additional aspects of the present invention are described in the paragraphs that follow and are illustrated in the accompanying drawings.

BRIEF DESCRIPTION OF THE DRAWINGS

FIG. 6 is an enlarged side cross-sectional view of one of the replica teeth, one of the appliances, and one of the stop members depicted in FIG. 5, and additionally showing a quantity of matrix material that has been placed between the replica and the tray shown in FIG. 4 after the replica and the tray have been inverted to make a transfer apparatus;

FIG. 7 is an enlarged side cross-sectional view illustrating the act of applying the transfer apparatus to one of the patient's teeth;

DETAILED DESCRIPTION OF THE PREFERRED EMBODIMENTS

Figure 1:
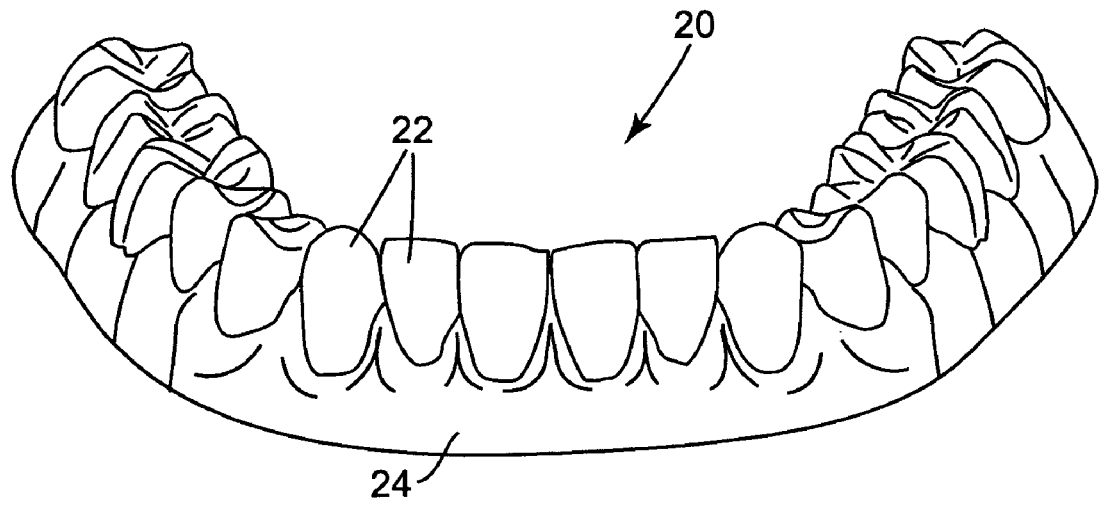
FIG. 1 is a top and front view showing a physical replica of one dental arch of an orthodontic patient, illustrating an example of a replica of a patient's tooth structure and adjacent gingival tissue as they might appear before the commencement of treatment.

A method for indirect bonding of one or more orthodontic appliances in accordance with one aspect of the present invention is depicted in FIGS. 1-7. FIG. 1 illustrates a replica 20 of a portion of a dental arch of an orthodontic patient. For exemplary purposes, the replica 20 represents the patient's lower dental arch. However, a replica of a patient's upper dental arch may be provided as an addition to or as an alternative to the lower dental arch replica as shown. As a further option, the replica 20 may represent only a portion of a dental arch, such as a quadrant of an arch or only one or two teeth of a dental arch. In the example illustrated, the replica 20 includes a number of replica teeth 22, corresponding to each tooth of the patient's lower dental arch.

As one option, the replica 20 is made by first taking an impression of the patient's lower dental arch, using care to avoid undue distortion. An alginate impression material may be used, such as "Palgat" Plus brand alginate impression material from 3M Espe. Alternatively, a hydrocolloid or vinyl polysiloxane impression material may be used, such as "Position Penta" brand vinyl polysiloxane impression material from 3M ESPE.

The model or replica 20 is then made from the impression. Optionally, the replica 20 is a "stone" model made from plaster of Paris, using care to avoid bubbles in the model. If small voids are present, the voids can be filled with a small, additional quantity of plaster of Paris. As an option, the replica 20 includes only the replica teeth 22 and sufficient replica gingival tissue 24 to hold the replica teeth 22 together.

As an alternative, the replica 20 may be made using digital data that is representative of the patient's teeth and adjacent gingival tissue. The digital data may be obtained by use of a hand-held intra-oral scanner or other device known in the art. As another option, the digital data may be obtained by scanning an impression or a stone model. The replica 20 may then be made from the digital data using, for example, a stereo lithographic printer.

The replica 20 may also be made using digital data in conjunction with a milling process. For example, a CNC milling machine, similar to the CAD/CIM milling machines sold by Cerec Network of Buelach, Switzerland, may be used to mill replicas made of ceramic, composite or other materials. An intra-oral camera, similar to the cameras associated with the Cerec machines, may be used to obtain digital data representing the shape of the dental arches. Alternatively, a scanner may be used to scan an impression or a model of an impression to obtain the digital data.

Preferably, the replica 20 is an accurate representation of the patient's oral structure. In particular, the replica teeth 22 will have a configuration and orientation that are identical to the configuration and orientation of the corresponding teeth of the orthodontic patient. In addition, the replica gingival tissue 24 will have a shape that matches the shape of the corresponding portions of the gingival tissue of the patient.

A thin layer of a release agent is then applied to the replica 20 and allowed to dry. An example of a suitable release agent is a water soluble polyvinyl alcohol, such as "PA0810" from PTM & W Company of Santa Fe Springs, Calif.

Figure 2:
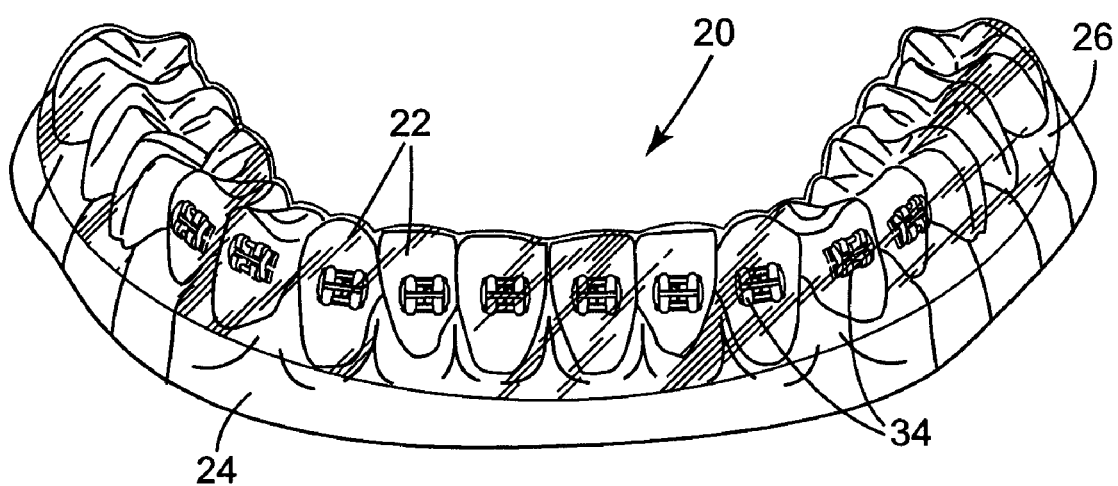
FIG. 2 is a view of the dental arch replica shown in FIG. 1, along with a set of orthodontic appliances and spacer material that have been applied to the replica.
Figure 3:
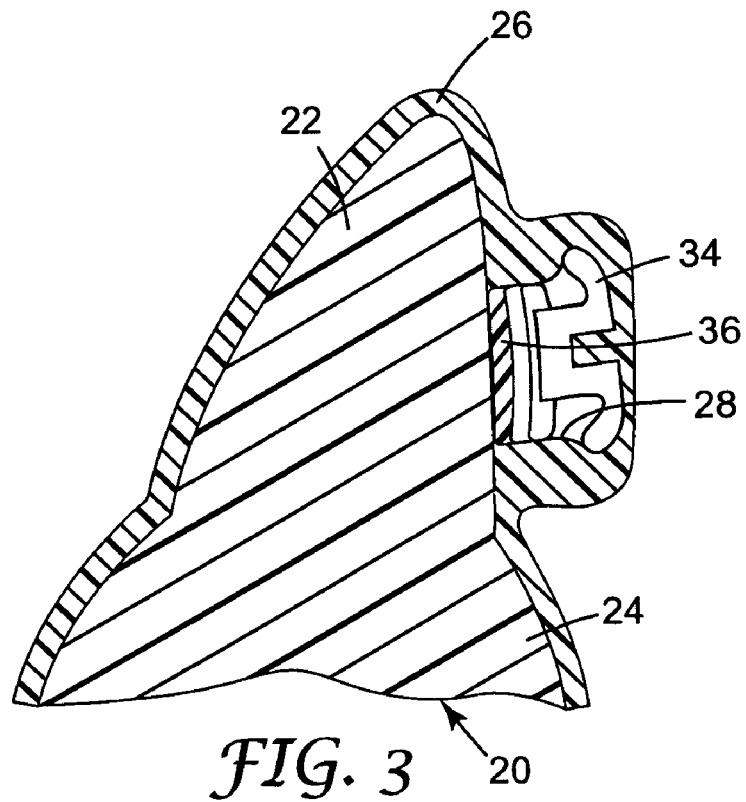
FIG. 3 is an enlarged side cross-sectional view of one of the replica teeth illustrated in FIG. 2 along with the appliance and spacer material.

Next, and as shown in FIGS. 2 and 3, a spacer material 26 is applied to the replica 20.

The spacer material 26 preferably comprises a custom-made material that is optionally formed using a rapid prototyping method. Examples of suitable rapid prototyping methods include stereolithography, thermojet printing and the like. Preferably, digital data representing the shape of a portion of the patient's dental arch is used in the rapid prototyping method to make the spacer material 26.

The spacer material 26 includes a number of pockets or cavities 28, each of which has a shape adapted to complementally receive a corresponding orthodontic appliance 34. For example, if an orthodontic bracket is intended to be received in one of the cavities 28, such cavity 28 optionally has an occlusal wall portion, a mesial wall portion, a gingival wall portion, a distal wall portion and a facial wall portion that match the configuration of the occlusal side, the mesial side, the gingival side, the occlusal side and the facial side respectively of the bracket. As another option, the gingival wall portion may be omitted to facilitate subsequent removal of the transfer apparatus from the patient's dental arch. Preferably, the cavities 28 include small protrusions that extend into and are complementally received in an archwire slot, a vertical slot between tiewings, and/or other features of the appliance. The cavities 28 are constructed slightly smaller than the corresponding appliance 34 in order to each firmly hold the orthodontic appliance 34 in place. However, the spacer material 26 is sufficiently flexible to enable the appliance 34 to be released from the cavity 28 when desired.

Each of the cavities 28 is positioned in a location that corresponds to the subsequent desired location of an orthodontic appliance 34 on the dental arch. For instance, each of the cavities 28 may be positioned to place the center of the appliance 34 in a location corresponding to the facial axis point (or "FA" point) of the corresponding replica tooth 22, although other locations are also possible. As will be described below, the spacer material 26 functions to subsequently provide clearance in the transfer apparatus for receiving the orthodontic appliances 34.

Preferably, the locations of the cavities 28 and consequently the ultimate position of the placed appliance 34 are determined by computer software that has access to digital data representing a virtual model of the replica 20. The software preferably includes subprograms suitable to analyze the existing malocclusion of the patient and select proper appliances 34 for treatment of the particular malocclusion at hand. Once the appliances 34 are selected and the locations of the cavities 28 for receiving the appliances are determined, the software instructs automated apparatus (such as apparatus using the rapid prototyping method mentioned earlier) to make the spacer 26 in custom fashion. Optionally, the software enables the practitioner, patient or other observer to see on a monitor or other video output a virtual representation of the patient's teeth as they should appear at the conclusion of treatment using the selected appliances 34 placed on certain locations of the teeth.

Preferably, the software includes subprograms for selecting appliances 34, analyzing malocclusions and/or predicting tooth movement and final positions of the teeth. An example of software for choosing appliances 34 is described in published U.S. patent application No. 2003/0163291, Aug. 28, 2003 entitled "Selection of Orthodontic Brackets", the disclosure of which is expressly incorporated by reference herein. Optionally, the software includes subprograms for making custom orthodontic appliances 34 using, for example, a computer numerical control milling machine, instead of selecting appliances 34 from an existing set of appliances as mentioned above. As an additional option, an orthodontic archwire may be placed in the slots of the appliances 34 and ligated in place. This step serves to further reduce the patient's time that is subsequently spent in the chair.

Preferably, the spacer material 26 extends over at least a majority of the facial surface area, the occlusal surface area and the lingual surface area of the replica teeth 22. However, the spacer material 26 may be omitted from contacting certain surfaces of the replica teeth 22 if desired, such as the lingual surface area of the replica teeth 22. In the illustrated embodiment, the spacer material 26 extends over the replica gingival tissue 24 as well as the lingual tooth areas.

Preferably, the spacer material 26 is provided as an integral unitary section of material, such that separate handling of the two or more sections of material is avoided. However, other constructions are also possible. For example, the spacer material 26 could comprise a number of discrete, ring-shaped sections of material that each receive a corresponding appliance, along with an initially separate preformed sheet of overlay material that is placed over each ring-shaped section of material once the ring-shaped sections are placed on the replica teeth 22.

The spacer material 26 can be any one of a number of materials such as a thermoset material. A suitable material is a silicone material, such as "RTV 615" from General Electric. Other suitable materials include, for example, materials used in rapid prototyping processes, such as thermoplastics (including nylons), thermoplastic elastomers and composites (e.g., glass-filled nylons). Examples of such materials include "Sinterstation HiQ Series SLS System" brand materials (including DuraForm brand PA polyamide nylon, DuraForm Brand GF glass-filled nylon, and Somos brand 201 materials), "Viper SLA" brand materials from 3D Systems (including Dreve Otoplatik Fototec brand SL materials and Accura brand SL materials), and "Thermojet" brand materials (including Thermojet brand 88 and Thermojet brand 2000 materials). Optionally, the spacer material 26 may be temporarily held in place on the replica 20 by use of an adhesive, such as a pressure sensitive adhesive. Preferably, the spacer material 26 is preformed and has the shape of the underlying replica dental arch when the spacer material 26 is relaxed. Alternatively, the spacer material 26 is formed to match the shape of the replica dental arch when it is applied to the latter. Optionally, the spacer material 26 is coated with a layer of pressure sensitive adhesive on one side and initially connected to a sheet of release material until such time as it is needed for use.

An orthodontic appliance 34 is received in each cavity 28 of the spacer material 26. In the embodiment illustrated in FIGS. 1-7, the orthodontic appliance 34 is a bracket, although other appliances such as buccal tubes, lingual sheaths, buttons and bondable bite openers are also possible. The appliances 34 may be placed in the cavities 28 either before or after the spacer material 26 is placed in contact with the replica dental arch. However, if the appliances 34 are placed in the cavities 28 after the spacer material 26 is applied to the replica dental arch, the facial sides of the cavities 28 are initially open and the spacer material 26 preferably includes an initially separate preformed sheet of overlay material that covers the facial sides of the cavities 28 and the appliances 34.

Before the appliances 34 are placed over the replica dental arch, a quantity of a composition 36 is placed between each appliance and the corresponding replica tooth 22. Preferably, the composition 36 is a light-curable composition such as a light-curable adhesive, and the adhesive is coated across the base of each appliance 34. Preferably, the appliances 34 are adhesive precoated appliances that have a layer of light-curable adhesive applied by the manufacturer to the base of each appliance 34. Such adhesive coated appliances are described in U.S. Pat. Nos. 5,015,180, 5,172,809, 5,354,199 and 5,429,229, all of which are assigned to the assignee of the present invention. The appliances 34 may be made of any suitable material such as metal (e.g., stainless steel), ceramic (e.g., translucent polycrystalline alumina) or plastic (e.g., translucent polycarbonate).

If the appliances 34 are not precoated with adhesive by the manufacturer, a coating of composition 36 such as an orthodontic adhesive may be applied by the practitioner to the base of each appliance 34. Suitable orthodontic adhesives include composites, compomers, glass ionomers and resin-modified glass ionomers. Examples of light-curable adhesives include Transbond XT brand or Transbond LR brand adhesives from 3M Unitek. Examples of chemical curing adhesives include Concise brand adhesive and Multi-Cure brand glass ionomer cement from 3M Unitek.

Next, the practitioner applies firm pressure to each appliance 34 in order to ensure that each appliance 34 is firmly seated on the corresponding replica tooth 22. The practitioner may apply finger pressure directly to the facial side of the appliances 34. Alternatively, if the facial side of the appliances 34 is not covered by the spacer material, the practitioner may use a scaler or other hand instrument to apply force to the archwire slot of each appliance 34.

Alternatively, the appliances 34 may be placed on the replica teeth 22 by means of robotic equipment. For example, the robotic equipment may include a gripping arm that is programmed to pick an appropriate appliance 34 from a set of appliances and place the selected appliance 34 on the appropriate replica tooth 22. The robotic arm then proceeds to grasp another appliance 34 for placement on another replica tooth 22. Finally, the spacer material 26 is placed over the appliances 34 and the replica arch 20.

The adhesive is shown in FIGS. 3-4 and 6-7 and is not necessarily drawn to scale. Initially, the adhesive 36 is only slightly hardened such that a tack cure is provided. In this manner, the appliances 34 will remain bonded to the replica teeth 22 when the spacer material 26 is subsequently removed, and yet the adhesive flash that extrudes from the sides of the appliance base remains relatively soft and can be removed without undue effort.

Figure 4:
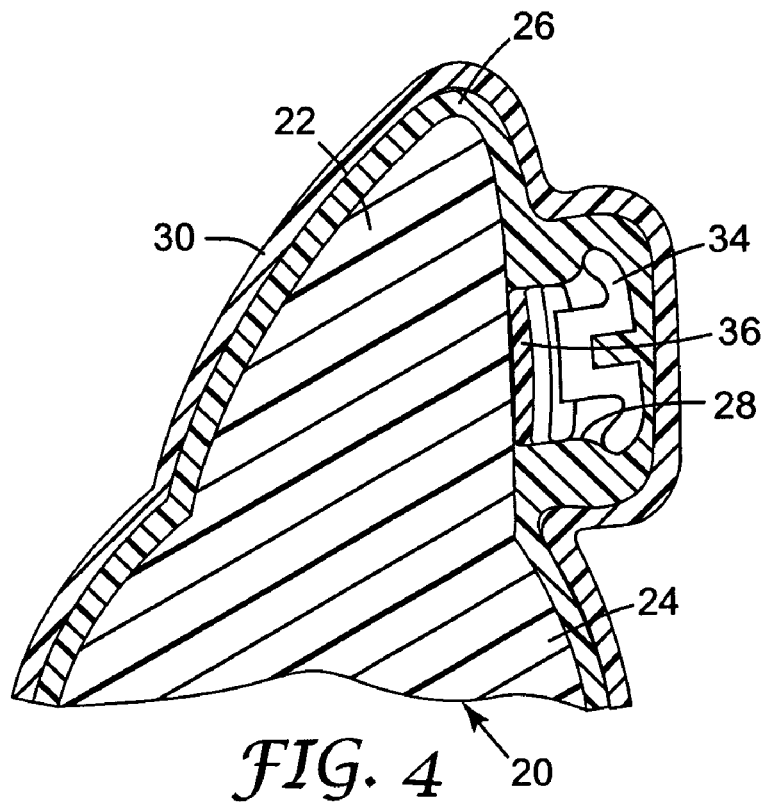
FIG. 4 is a view somewhat similar to FIG. 3, additionally showing a tray that has been formed over the spacer material.
Figure 5:
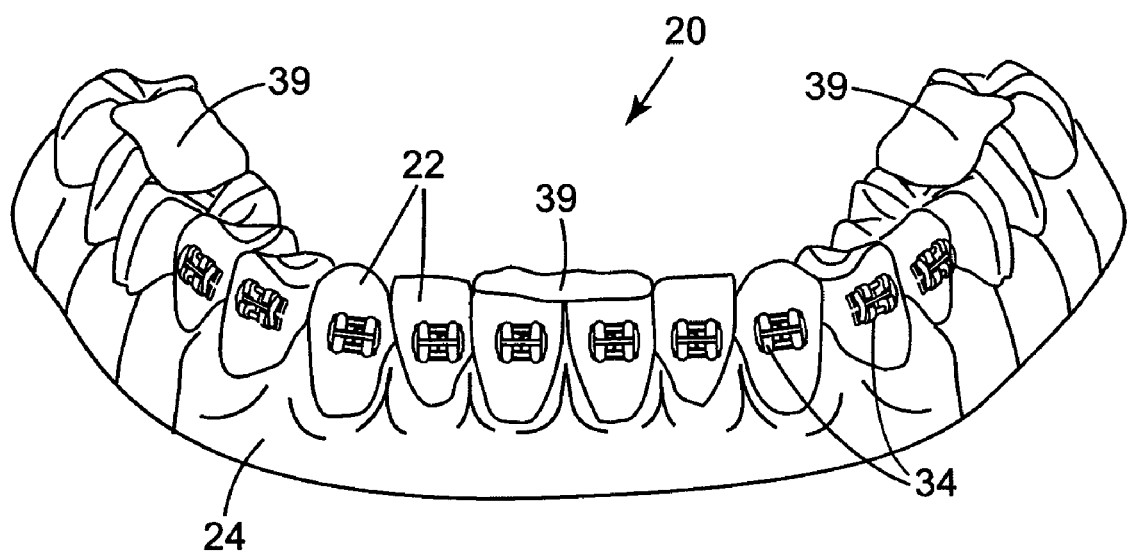
FIG. 5 is a view of the tooth structure replica illustrated in FIG. 1 after the spacer material and the tray have been detached from the replica, and additionally showing three stop members that have been placed along occlusal sections of the replica teeth.

Subsequently, a tray 30 is formed over the spacer material 26 as illustrated in FIG. 4. Preferably, the tray 30 is shaped by vacuum forming a sheet of material over the sheet of spacer material 26. A suitable material for the tray 30 is a sheet of polycarbonate such as Makrolon brand material from Bayer or Lexan brand polycarbonate from GE having a thickness of 0.06 inch. Other materials, such as polyethyleneterephthalate glycol ("PETG") may also be used. Heat is applied during the vacuum forming process in order to facilitate conformance of the sheet to the external configuration of the spacer material 26.

Once the tray 30 has hardened, the tray 30 is detached from the spacer material 26. The spacer material 26 is then detached from the replica 20 and the appliances 34 and set aside or discarded. During detachment of the spacer material 26 from the replica 20, the appliances 34 remain bonded to the replica teeth.

After the flash from excess adhesive 34 is removed from areas adjacent the base of the appliances 34, the remaining adhesive is more fully cured. As one example, if the appliances 34 are made of metal or other opaque material and if a light-curable adhesive 36 is used, it is preferable to expose the replica 20 to the curing light for a relatively long amount of time such as 3 to 5 minutes to ensure that the adhesive 36 has sufficiently hardened. As an alternative to light curing chambers, a hand-held curing unit may be used, such as Ortholux XT brand curing unit from 3M Unitek.

As an additional option, the replica 20 including the replica teeth 22 may be made from a material that transmits actinic radiation. Suitable materials include epoxy resins that are transparent or translucent when hardened. Preferably, the material is optically clear. An example of a suitable epoxy is E-CAST F-82 clear epoxy resin and No. 302 (or UCE-302) hardener, from United Resin Corporation. Other suitable materials include polyesters and urethanes. The use of transparent or translucent materials is advantageous in instances where the appliances 34 are made of opaque materials, since the actinic radiation can be transmitted through the replica 20 for curing portions of the adhesive 36 that are located adjacent the middle of the appliance base. Actinic radiation can include wavelengths in the visible range, ultraviolet range, infrared range or any combination thereof, in accordance with the type of photoinitiator contained in the adhesive 36.

Excess portions of the tray 30 are then trimmed as desired. Next, stop members 39 are formed to facilitate subsequent positioning of the transfer apparatus relative to the patient's teeth during a bonding procedure. The stop members 39 may be made by placing curable material on the replica 20 or alternatively within the channel of the tray 30. In the illustrated embodiment, three spaced-apart stop members 39 are made by placing curable material across occlusal sections of the replica dental arch 20. One stop member 39 is formed near the center of the replica dental arch 20, while the other two stop members 39 are formed near the right end and left end respectively of the replica dental arch 20. However, other constructions are possible. For example, a single stop member 39 may be provided that extends along a substantial majority of the curved longitudinal axis of the replica dental arch 20. Alternatively, two stop members 39 may be provided, each of which extends along a majority of the left quadrant and the right quadrant respectively of the replica dental arch 20 and follows the curved longitudinal axis of the arch. Additionally, or as an alternative to occlusal stop members, one or more stop members 39 may be provided along the lingual surfaces and/or the facial surfaces of the replica dental arch 20. Lingual and facial stop members may be particularly advantageous to ensuring proper fitting and placement of the transfer apparatus in instances when the patient's maloccluded teeth present diverging tooth angulations.

The stop members 39 may be made from a variety of materials. Suitable materials include, for example, an orthodontic or dental adhesive, a dental restorative material, or a bite registration material. An example of a suitable bite registration material is "Imprint Bite" bite registration material from 3M Espe. Preferably, the stop members 39 are made of a thermosetting material that, after hardening, does not substantially soften upon contact with heat. Preferably, the stop members 39 transmit actinic radiation and retain their shape over extended periods of time.

Next, the tray 30 is placed over the replica dental arch 20 including the unhardened stop members 39. The tray 30 is pressed toward the replica arch 20 with sufficient force to deform the shape of the unhardened stop members 39 and bring the tray 30 to a desired position relative to the replica 20 as the stop members 39 are flattened. This desired position is somewhat adjacent the replica 20, but is sufficiently spaced from the replica 20 so that a quantity of matrix material may be received between the tray 30 and the replica 20 as described below. The stop members 39 are then allowed to harden. Once hardened, the stop members 39 have a gingival or tooth-facing surface that matches the occlusal surface of the facing occlusal section of the replica tooth or teeth 22.

A matrix material is then applied, either to the replica 20 or to the channel of the tray 30. For example, if the matrix material is relatively viscous and resembles a semi-liquid or gel, the matrix material may be applied to the replica 20 as it appears in FIG. 5, using a syringe, brush or other technique. Alternatively, if the matrix material has a relatively low viscosity and resembles a liquid, it may be preferable to invert the tray 30 such that the open side of the channel of the tray 30 is facing upwardly as shown in FIG. 6. If the tray 30 is inverted, the tray 30 is not initially trimmed along the outermost distal sides (corresponding to the ends of the dental arch) so that the liquid matrix material is contained within the tray channel.

Subsequently, the replica 20 is positioned in the tray 30 such that the matrix material 40 is received in the channel of the tray 30 and between the tray 30 and the replica 20. As shown in FIG. 6, the matrix material 40 surrounds the appliance 34 and also extends along the labial and lingual surfaces of the replica tooth 22. Moreover, the matrix material 40 extends along the bottom and side wall surfaces of the tray 30. The stop members 39 serve to properly position the tray 30 from the external surfaces of the replica teeth 22 as the matrix material 40 is received in the tray channel. The matrix material 40 is then allowed to harden.

Preferably, the matrix material 40 surrounds each appliance 34 and the entire replica arch 20 except in areas near the stop members 39, which remain in contact with the occlusal sections of the replica 20. Preferably, the matrix material 40 and the stop members 39 chemically bond to each other as the matrix material 40 has hardened, so that the stop members 39 are not unintentionally detached during the subsequent steps.

Preferably, the matrix material 40 has a relatively low viscosity before hardening so that intimate contact between the matrix material 40 and each appliance 34 is assured. In this manner, the matrix material 40 is able to substantially penetrate in various recesses, cavities and other structural features of each appliance 34 so that a secure connection between the appliance 34 and the matrix material 40 can be established. An example of a suitable matrix material having a relatively low viscosity is a silicone material such as "RTV615" silicone material from General Electric as mentioned above. The relatively low viscosity of this silicone matrix material also assures that the matrix material will assume a configuration that closely matches the shape of the adjacent surfaces of the replica teeth 22.

Alternatively, the matrix material 40 may comprise a dental impression material or a bite registration material. Suitable materials include polyvinylsiloxane impression material, such as Memosil 2 brand vinyl polysiloxane material from Heraeus Kulzer Inc., or Peppermint Snap brand clear bite registration material from Discus Dental. If a light-curable adhesive is to be used for bonding the appliances 34 to the patient's teeth, the matrix material 40 is preferably optically clear and transmits actinic radiation without substantial absorption.

Once the matrix material 40 has hardened, the tray 30, together with the matrix material 40 and the appliances 34, are detached from the replica 20. The use of the release agent as mentioned above helps facilitate detaching of the appliances 34 from the corresponding replica teeth 22. Excess material of the tray 30 and excess matrix material 40 are then trimmed as desired as discarded. The resultant trimmed transfer apparatus 44 (comprising the tray 30, the matrix material 40, the stop members 39 and the appliances 34) is shown in cross-sectional view in FIG. 7.

Once the patient has returned to the office, the patient's teeth that are to receive appliances are isolated using cheek retractors, tongue guards, cotton rolls, dry angles and/or other articles as needed. The teeth are then thoroughly dried using pressurized air from an air syringe. Etching solution (such as 3M Unitek Transbond XT brand etching gel) is then dabbed onto the teeth in the general area that is to be covered by the appliances 34, taking care to prevent the etching solution from flowing into interproximal contacts or engaging the skin or gingiva.

After the etching solution has remained on the selected tooth surfaces for a period of approximately thirty seconds, the solution is rinsed away from the teeth with a stream of water for fifteen seconds. The patient's teeth are then dried by the application of pressurized air from an air syringe (for example, for a time period of thirty seconds) and excess water is removed by suction. Care should also be undertaken to ensure that the saliva does not come in contact with the etched enamel surfaces. Cotton rolls and other absorbent devices are replaced as needed, again making sure that saliva does not contact the etched enamel. Air from the air syringe may then be applied to the teeth again to ensure that the teeth are thoroughly dried.

Next, a bonding adhesive is applied to the hardened adhesive 36 and/or the selected areas of the patient's teeth. Optionally, the adhesive is a two-component adhesive as depicted in FIG. 7. For example, the first component 41 is a Transbond brand XT moisture insensitive primer, and the second component 43 is Transbond brand Plus self-etching primer, both from 3M Unitek. The first component 41 is applied to the hardened adhesive 36 and the second component 43 is applied to the area of the patient's tooth that is to receive the appliance 34. In FIG. 7, the patient's tooth is designated by the numeral 42.

After the first component 41 has been applied to the hardened adhesive 36 and the second component 43 has been applied to the corresponding area of the patient's tooth 42, the tray 30 is then positioned over the corresponding teeth and seated, optionally with a swinging, hinge-type motion. Since the shape of the cavity of the matrix material 40 and the stop members 39 together match the shape of the underlying teeth, the appliances 34 are simultaneously seated against the underlying teeth 42 at precisely the same locations corresponding to the previous position of the appliances 34 on the replica 20. Preferably, the tray 30 has a shape that is complemental to the patient's tooth structure, and has sufficient stiffness to press the appliances 34 against the teeth 42 as the adhesive cures without the application of external pressure. However, as an option, external pressure may also be applied to the occlusal, labial and buccal surfaces of the tray 30 until such time as the bonding adhesive has sufficiently hardened. For example, finger pressure may be used to firmly press the appliances 34 against the enamel surfaces of the patient's teeth 42.

Other examples of suitable two-component chemical curing adhesives include Sondhi brand Rapid-Set indirect bonding adhesive, Unite brand adhesive and Concise brand adhesive, all from 3M Unitek. Alternatively, a resin-modified glass ionomer cement may be employed.

Once the bonding adhesive has hardened, the tray 30 is carefully removed from the patient's dental arch. Preferably, the tray 30 is first separated from the matrix material 40, which remains in place over the dental arch along with the appliances 34. Next, the matrix material 40 is detached from the appliances 34. Optionally, a hand instrument such as a scaler may be used to help hold each appliance 34 against the surface of the respective tooth 42 of the patient as the matrix material 40 is peeled away from the appliances 34. However, in instances where a relatively soft matrix material is employed or otherwise readily releases from the appliances 34, the use of a scaler to help avoid fracturing the fresh adhesive bond is optional.

As another option, the tray 30 may be separated from the matrix material 40 before the bonding adhesive has hardened. This option is particularly useful when the bonding adhesive is a light-curable adhesive.

Once the matrix material 40 has been detached from the appliances 34, an archwire is placed in the slots of the appliances 34 and ligated in place. Suitable ligation devices include tiny, elastic O-rings as well as sections of wire that are tied in a loop around the appliances 34. As another option, the appliances 34 may be self-ligating appliances that include a latch for releasably engaging the archwire such as those described in U.S. Pat. No. 6,302,688 and PCT Publication No. WO02/089693.

As can be appreciated, the hardened adhesive 36 provides a contoured bonding surface for the base of the corresponding appliance 34. The configuration of this bonding surface closely matches the shape of the patient's tooth surface and consequently facilitates the subsequent bond (using the bonding adhesive components 41, 43) that is established between the appliance 34 and the tooth 42. The bonding surface reduces the likelihood that the appliance 34 will become unintentionally detached from the tooth during the course of treatment.

The use of the spacer material 26 in combination with the stop members 39 in the method described above is a significant advantage in that an appropriate region for receiving matrix material 40 in the tray 30 is provided. The spacer material 26 and the stop members 39 can be shaped as needed to provide precisely the volume and configuration of region as may be desired. For example, the spacer material 26 and the stop members 39 may help ensure that a uniform thickness of matrix material is subsequently provided around the substantial extent of the tooth 42 with the exception of the areas adjacent the appliance 34 and the occlusal section of the dental arch adjacent the stop members 39.

Moreover, the use of the spacer material 26 facilitates the use of a matrix material having a relatively low viscosity, such as a matrix material having a liquid consistency. The tray 30 is relatively stiff, and consequently maintains its shape during forming of the matrix material 40. The transfer apparatus 44 is constructed such that the tray 30 (other than the stop members 39) does not directly contact the patient's teeth or gingival tissue. Instead, only the matrix material 40 and the stop members 39 come into contact with the patient's teeth.

Another advantage of the present invention is that the relatively soft matrix material 40 is flexible and can accommodate a limited amount of tooth movement. For example, the teeth of the patient may have slightly shifted between the time that the impressions are taken and the time that the transfer apparatus 44 is fitted in the patient's oral cavity for bonding the appliances 34. The matrix material 40 has sufficient flexibility to comply with small shifts or adjustments in the patient's tooth positions, so that the appliances 34 are properly bonded to the intended, predetermined locations on the patient's tooth.

The matrix material 40 preferably has a viscosity before curing that is less than about 60,000 cp. More preferably, the matrix material 40 has a viscosity before curing that is less than about 25,000 cp. Most preferably, the matrix material 40 has a viscosity before curing that is less than about 8000 cp. Once hardened, the matrix material 40 has a Shore A hardness that is in the range of about 10 to about 80, more preferably in the range of about 30 to about 60 and most preferably in the range of about 40 to about 50.

The stop members 39 are relatively inflexible and have a Shore A hardness that is greater than the Shore A hardness of the matrix material 40. Preferably, the stop members 39 have a Shore A hardness that is greater than about 60 and more preferably is greater than about 90.

The use of the spacer material 26 enhances control over construction of the transfer apparatus, including the resultant shape of the tray 30 and the contained matrix material 40. For instance, the spacer material 26 enables the resultant thickness of the matrix material 40 to be relatively uniform and preferably relatively thin. This uniform thickness of relatively small dimension facilitates curing of a photocurable adhesive used to bond the appliances to the patient's teeth. Specifically, when a light-curable adhesive is used to bond the appliances 34 to the patient's teeth, the uniform thickness of matrix material 40 helps to ensure that the light-curable adhesive beneath each appliance 34 is sufficiently cured to the same extent from one appliance 34 to the next. In this manner, the user need not compensate for varying thicknesses of matrix material and the curing times associated with each quantity of adhesive need not vary from one appliance 34 to the next.

Figure 8:
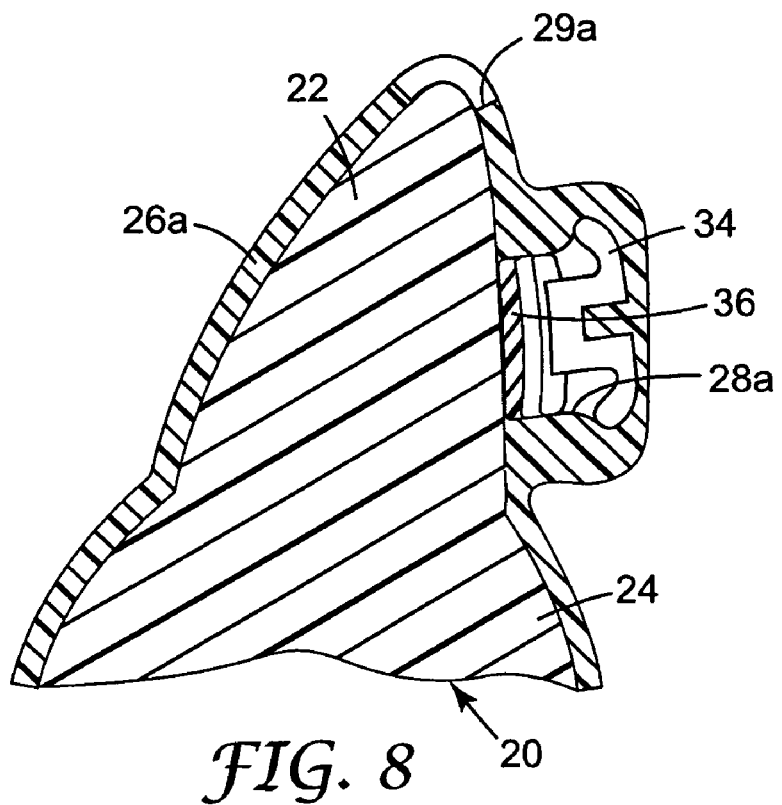
FIG. 8 is a view somewhat similar to FIG. 3 but in accordance with another embodiment of the present invention.
Figure 9:
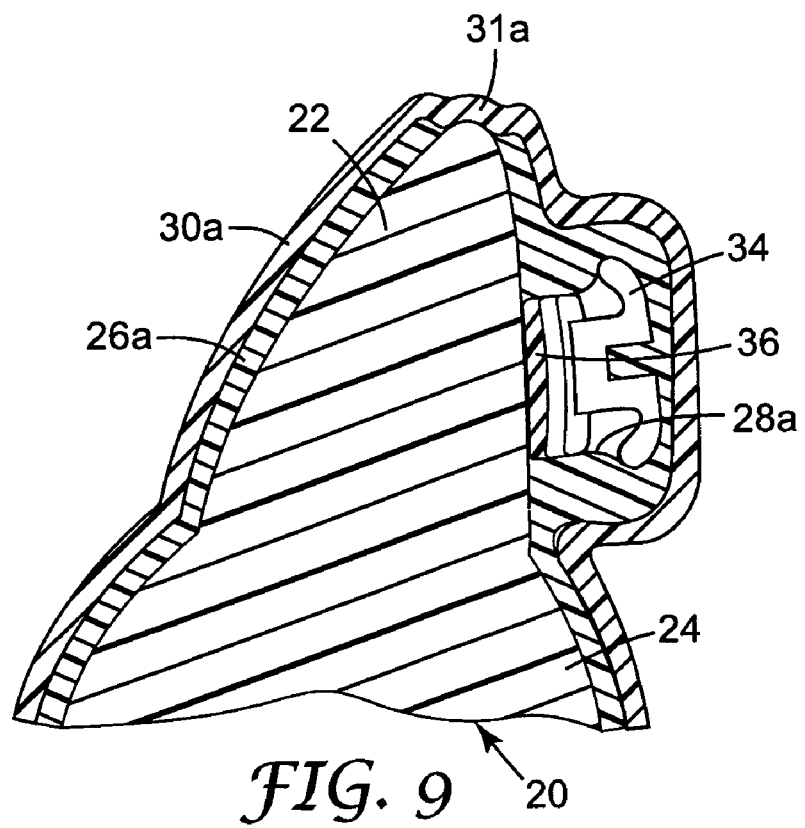
FIG. 9 is a view somewhat similar to FIG. 4 but in accordance with the embodiment illustrated in FIG. 8.

Another embodiment of the invention is illustrated in FIGS. 8 and 9. Except as described below, this embodiment is identical to the embodiment set out above in connection with FIGS. 1-7.

In the embodiment illustrated in FIGS. 8 and 9, a spacer material 26a is similar to the spacer material 26 except that the spacer material has one or more openings 29a that extend along the occlusal sections of the replica teeth 22. For example, the spacer material 26a may have three openings 29a that are located (with respect to the replica 20) in approximately the same positions as the stop members 39 shown in FIG. 5. An interconnecting web (not shown) of the spacer material 26a extends between adjacent openings 29a and over remaining regions of the occlusal sections of the replica teeth 22. The spacer material 26a also includes cavities (such as cavity 28a) that are similar to the cavities 28 described above.

Subsequently, a tray 30a is formed over the spacer material 26a (including over the openings 29a) as shown in FIG. 9. This forming process is essentially the same as the forming process described in connection with FIG. 4, except that in this instance a portion of the tray material is drawn into the openings 29a and contacts the adjacent, occlusal sections of the replica teeth 22. Each of these portions that are drawn into the openings 29a provides a stop member 31a that, in use, functions in a manner similar to the stop members 39 set out above. However, since the stop members 31a are integrally connected to a bottom wall portion of the tray 30a and together form a single, unitary body, the handling of separate components during assembly of the transfer apparatus is eliminated.

A variety of other embodiments are also possible and will be apparent to those skilled in the art. For example, a bonding composition may be applied to the base of each appliance 34 by the manufacturer and then packaged in a container for shipment to the practitioner, as described in pending U.S. patent application Ser. No. 10/678,286 entitled "Apparatus for Indirect Bonding of Orthodontic Appliances and Method of Making the Same". As a result, the practitioner can simply remove the transfer apparatus from the container and immediately place the appliances on the patient's teeth. Additionally, the bonding composition of at least one appliance 34 may differ from the bonding composition of at least one other appliance 34 in the transfer apparatus in terms of composition, properties or characteristics, as described in pending U.S. patent application Ser. No. 10/742,561 entitled "Packaged Orthodontic Assembly with Adhesive Precoated Appliances", such that the bonding composition can be tailored to enhance the bond between the particular selected appliance 34 and its intended tooth.

Additionally, the transfer apparatus may be used for bonding only a single appliance to a patient's tooth. For example, a portion of the transfer apparatus described above may be used to bond a single appliance to a single tooth subsequent to the time that other appliances are bonded, such as in instances where access to the tooth is initially hindered by other teeth. As another example, a portion of the transfer apparatus described above may be used to re-bond an appliance that has unintentionally debonded from the tooth, or to bond a new appliance to a tooth to replace the original appliance.

All patents, patent applications and other publications identified herein are expressly incorporated by reference into this disclosure. Moreover, a number of other variations, modifications and additions are also possible without departing from the spirit of the invention. Accordingly, the invention should not be deemed limited to the specific embodiments described above, but instead only by a fair scope of the claims that follow and their equivalents.

The invention claimed is:

1. Transfer apparatus for use in indirect bonding of orthodontic appliances comprising:
    a tray having a channel;
    a matrix material received in the channel;
    at least one orthodontic appliance detachably connected to the matrix material, wherein the matrix material has a first Shore hardness;
    at least one stop member located next to the channel, wherein each of the at least one stop member comprises a polymeric thermoset material having a second Shore hardness that is greater than the first Shore hardness and extends next to the matrix material for contact with the dental arch; and
    a chemical bond affixing each stop member to the matrix material.

2. Transfer apparatus for use in indirect bonding of orthodontic appliances according to claim 1 wherein the tray includes a side wall portion and a bottom wall portion adjacent the channel, and wherein the matrix material extends across at least part of the side wall portion.

3. Transfer apparatus for use in indirect bonding of orthodontic appliances according to claim 1 wherein each of the at least one stop member has a thickness that is approximately equal to the thickness of adjacent regions of the matrix material.

4. Transfer apparatus for use in indirect bonding of orthodontic appliances according to claim 1 wherein the transfer apparatus includes at least two stop members, and wherein each of the at least two stop members has an outer wall portion for contact with an occlusal section of a dental arch.

5. Transfer apparatus for use in indirect bonding of orthodontic appliances according to claim 4 wherein each outer wall portion has a configuration complemental to the respective occlusal section of the dental arch.

6. Transfer apparatus for use in indirect bonding of orthodontic appliances according to claim 4 wherein each of the at least two stop members are spaced apart from one another.

7. Transfer apparatus for use in indirect bonding of orthodontic appliances according to claim 6 wherein the channel of the tray includes a curved longitudinal axis, and wherein the transfer apparatus includes three stop members spaced along the longitudinal axis.

8. Transfer apparatus for use in indirect bonding of orthodontic appliances according to claim 1 wherein the channel has a curved longitudinal axis, and wherein each of the at least one stop member extends along at least a majority of the length of the channel.

9. Transfer apparatus for use in indirect bonding of orthodontic appliances according to claim 1 wherein each of the at least one stop member is integrally connected to the tray.

10. Transfer apparatus for use in indirect bonding of orthodontic appliances according to claim 1 wherein the matrix material is a curable material and has a viscosity before curing that is less than about 60,000 cp.

11. Transfer apparatus for use in indirect bonding of orthodontic appliances according to claim 1 wherein the matrix material is a curable material and has a viscosity before curing that is less than about 25,000 cp.

12. Transfer apparatus for use in indirect bonding of orthodontic appliances according to claim 1 wherein the first Shore hardness is a Shore A hardness that is in the range of about 10 to about 80.

13. Transfer apparatus for use in indirect bonding of orthodontic appliances according to claim 1 wherein the first Shore hardness is a Shore A hardness that is in the range of about 30 to about 60.

14. Transfer apparatus for use in indirect bonding of orthodontic appliances according to claim 1 wherein the tray has a facial side wall portion, a lingual side wall portion and a bottom wall portion adjacent the channel, and wherein each of the at least one stop member is connected to the lingual side wall portion.

15. Transfer apparatus for use in indirect bonding of orthodontic appliances according to claim 1 wherein the tray has a facial side wall portion, a lingual side wall portion and a bottom wall portion adjacent the channel, and wherein each of the at least one stop member is connected to the facial side wall portion.

16. Transfer apparatus for use in indirect bonding of orthodontic appliances according to claim 1 wherein the tray has a facial side wall portion, a lingual side wall portion and a bottom wall portion adjacent the channel, and wherein each of the at least one stop member is connected to the bottom wall portion.

17. A method of orthodontic indirect bonding comprising:
providing an orthodontic transfer apparatus comprising a tray, a quantity of matrix material received in the tray, and one or more orthodontic appliances detachably connected to the matrix material, wherein the matrix material has a first Shore hardness;
moving the transfer apparatus into a patient's oral cavity in order to locate the one or more orthodontic appliances adjacent the patient's dental arch; and
engaging a thermoset polymeric material of the transfer apparatus with an occlusal section of the patient's dental arch as one or more of the appliances are brought into contact with the patient's dental arch, wherein the thermoset polymeric material has a second Shore hardness that is greater than the first Shore hardness of the matrix material.

18. A method of orthodontic indirect bonding according to claim 17 wherein the act of engaging a thermoset polymeric material of the transfer apparatus with an occlusal section of the patient's dental arch includes the act of engaging at least two spaced apart stop members of the transfer apparatus with an occlusal section of the patient's dental arch.

19. A method of orthodontic indirect bonding according to claim 17 wherein the first Shore hardness is a Shore A hardness that is in the range of about 10 to about 80.

20. A method of orthodontic indirect bonding according to claim 17 wherein the first Shore hardness is a Shore A hardness that is in the range of about 30 to about 60.

21. A method of orthodontic indirect bonding according to claim 17 wherein the matrix material is a curable material and has a viscosity before curing of less than about 60,000 cp.

22. A method of orthodontic indirect bonding according to claim 17 wherein the matrix material is a curable material and has a viscosity before curing of less than about 25,000 cp.

* * * * *